United States Patent [19]
Boyle et al.

[11] Patent Number: 5,613,981
[45] Date of Patent: Mar. 25, 1997

[54] BIDIRECTIONAL DUAL SINUSOIDAL HELIX STENT

[75] Inventors: William J. Boyle, Carlsbad; Rosalinda A. Wong, San Diego; James M. Shy, Chula Vista; Don H. Tran, Westminster, all of Calif.

[73] Assignee: Medtronic, Inc., Minneapolis, Minn.

[21] Appl. No.: 426,310

[22] Filed: Apr. 21, 1995

[51] Int. Cl.$^6$ ............................................. A61M 29/00
[52] U.S. Cl. ................................... 606/198; 606/195
[58] Field of Search .................... 623/1, 12; 606/192, 606/194, 195, 198

[56] References Cited

U.S. PATENT DOCUMENTS

| | | | |
|---|---|---|---|
| 4,649,922 | 3/1987 | Wiktor | 606/194 |
| 4,731,073 | 3/1988 | Robinson | 623/1 |
| 4,878,906 | 11/1989 | Lindemann et al. | 623/1 |
| 4,886,062 | 12/1989 | Wiktor | 606/194 |
| 4,969,458 | 11/1990 | Wiktor | 606/194 |
| 4,990,158 | 2/1991 | Kaplan et al. | 623/1 |
| 5,019,090 | 5/1991 | Pinchuk | 606/194 |
| 5,116,365 | 5/1992 | Hillstead | 623/1 |
| 5,133,732 | 6/1992 | Wiktor | 606/195 |
| 5,226,913 | 7/1993 | Pinchuk | 623/1 |
| 5,282,823 | 2/1994 | Schwartz et al. | 606/198 |
| 5,413,597 | 5/1995 | Krajicek | 623/12 |
| 5,476,508 | 12/1995 | Amstrup | 623/1 |

FOREIGN PATENT DOCUMENTS

| | | | |
|---|---|---|---|
| 2189159 | 10/1987 | United Kingdom | 623/1 |
| 9112779 | 9/1991 | WIPO . | |

Primary Examiner—Michael Powell Buiz
Assistant Examiner—Patrick W. Rasche
Attorney, Agent, or Firm—Dianne M. F. Plunkett; Harold R. Patton

[57] ABSTRACT

A method apparatus for a radially expandable stent for implantation within a body vessel, comprising a first wire formed winding and a second wire formed winding. The first wire formed winding has a hollow cylindrical shape including a preformed pattern such as a sinusoidal wave form and being wound into a continuous helix the length of the stent. The second wire formed winding has a hollow cylindrical shape including a preformed pattern such as a sinusoidal wave form and being wound into a continuous helix the length of the stent. The second winding helix is opposite that of the first winding helix. The second winding has a greater inner diameter than the outer diameter of the first winding. The second winding is coaxial with the first winding, the pattern of the first winding symmetrically intersects with the pattern of the second winding to form a uniform series of crossings thereby permitting even expansion of the first and second windings. The proximal end of the first winding may be attached to the proximal end of the second winding. The distal end of the first winding may be attached to the distal end of the second winding. An expandable member within the first winding to expand the first and second winding is included.

23 Claims, 4 Drawing Sheets

5,613,981

BIDIRECTIONAL DUAL SINUSOIDAL HELIX STENT

FIELD OF THE INVENTION

The present invention relates to intravascular stent implants for maintaining vascular patency in humans and animals and more particularly to a stent in the form of a bidirectional helix configuration of the sinusoidal wave form.

BACKGROUND OF THE INVENTION

Percutaneous transluminal coronary angioplasty (PTCA) is used to reduce arterial build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver or any other lumen of the body. The invention applies to acute and chronic closure or reclosure of body lumens.

A stent is a cylindrically shaped wire formed device intended to act as a permanent prosthesis. It has a plurality of metal elements joined to permit flexing of the cylindrical body along its longitudinal axis thereby conforming to a curved body lumen. A stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

Various shapes of stents are known in the art. U.S. Pat. No. 4,649,9221 to Wiktor for "Catheter Arrangement Having A Variable Diameter Tip and Spring Prothesis" discloses a linearly expandable spring-like stent. U.S. Pat. No. 4,886,062 to Wiktor for "Intravascular Radially Expandable Stent and Method of Implant" discloses a two-dimensional zig-zag form, typically a sinusoidal form. U.S. Pat. No. 4,969,458 to Wiktor for "Intracoronary Stent and Method of Simultaneous Angioplasty and Stent Implant" discloses a stent wire coiled into a limited number of turns wound in one direction then reversed and wound in the opposite direction with the same number of turns, then reversed again and so on until a desired length is obtained. U.S. Pat. No. 5,019,090 to Pinchuk for "Radially Expandable Endoprosthesis and the Like" discloses a plurality of adjacent generally circumferential sections that are substantially axially positioned with respect to each other. At least one of the generally circumferential sections has a generally circumferentially disposed expandable segment that imparts circumferential and radial expandability to the stent. U.S. Pat. No. 5,116,365 to Hillstead for a "Stent Apparatus and Method for Making" discloses a stent constructed from two elongated wires which are each bent into a series of tight bends. The two wires are permanently adhered at a first interconnection junction. The two wires are then wrapped around a mandrel repeatedly forming two opposing series of interconnections. U.S. Pat. No. 5,133,732 to Wiktor for "Intravascular Stent" discloses a stent body coiled from a generally continuous wire with a deformable zig-zag structure with a means for preventing the stent body from stretching along its longitudinal axis.

Stents have limited ability to provide effective patching of perforated vessels due to the spacing between metal elements. U.S. Pat. No. 4,878,906 to Lindeman et al. for "Endoprosthesis for Repairing a Damaged Vessel" describes an endoprosthesis made of a thin wall molded plastic sleeve intended to be collapsed radially and delivered to a damaged area of a vessel where it is expanded to provide a sealed interface to the vessel on its outer peripheral ends. The endoprosthesis therefore provides a patch which prevents leakage of blood from a vessel wall. The endoprosthesis disclosed employs various molded-in ribs, struts and the like to adapt the device for particular applications and to provide the desired degree of stiffness to form the sealed interface with the vessel wall. Such a stiff prosthesis, however, could not be expected to have the longitudinal flexibility needed to adapt to curved vessels.

In addition to limited ability to provide effective patching of perforated vessels due to the spacing between metal elements, such metal stents also have limited ability to carry and deliver drugs, such as antirestenosis drugs or anticoagulant drugs, to the site of an intravascular injury. WO 91/12779 to Wolff et al. for "Intralumenal Drug Eluting Prosthesis" suggests that antiplatelet agents, anticoagulant agents, antimicrobial agents, antimetabolic agents and other drugs could be supplied in polymeric stents to reduce the incidence of restenosis. U.S. Pat. No. 5,282,823 to Schwartz et al. for "Intravascularly Radially Expandable Stent" discloses a plurality of metal elements joined to allow flexing of the cylindrical body along the longitudinal axis of the body and a polymeric film extending between the metal elements of the stent.

SUMMARY OF THE INVENTION

It is an object of the invention to provide additional vessel coverage and increased hoop strength. It also is an object of the invention to provide a stent capable of patching leaking blood vessels. It is a further object of the invention to provide a stent capable of delivering therapeutic agents to a blood vessel.

The present invention, is accomplished by providing a method and apparatus for a radially expandable stent for implantation within a body vessel, comprising a first wire formed winding and a second wire formed winding. The first wire formed winding has a hollow cylindrical shape including a preformed pattern such as a sinusoidal wave form being wound into a continuous helix the length of the stent. The second wire formed winding has a hollow cylindrical shape including a preformed pattern such as a sinusoidal wave form being wound into a continuous helix the length of the stent. The second winding helix is opposite that of the first winding helix. The second winding has a greater inner diameter than the outer diameter of the first winding. The second winding is coaxial with the first winding, the pattern of the first winding symmetrically intersects with the pattern of the second winding to form a uniform series of crossings thereby permitting even expansion of the first and second windings. The proximal end of the first winding may be attached to the proximal end of the second winding. The distal end of the first winding may be attached to the distal end of the second winding. A means within the first winding to expand the first and second winding is included.

DETAILED DESCRIPTION OF THE PREFERRED EMBODIMENTS

Figure 1:
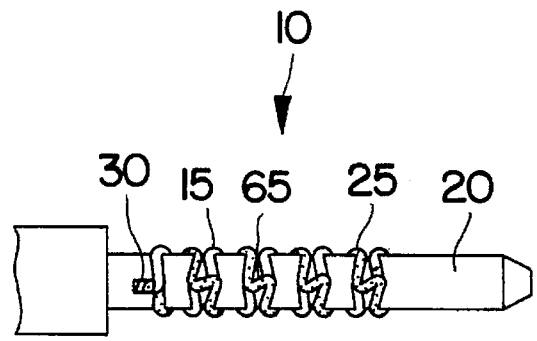
FIG. 1 is a side elevation view of a preferred embodiment of a stent being wound on a mandrel according to this invention.

Referring to FIG. 1, stent 10 is formed by winding a wire around a mandrel 20 into a preformed pattern such as a first sinusoidal wave form 15 helix. The outer diameter of the mandrel 20 can range from 0.175 inches to 0.065 inches depending on the balloon size to be used and most preferably a 0.100 inch outer diameter mandrel 20 which is suitable for the most common balloon sizes. A second preformed pattern such as a sinusoidal wave form 25 is then wound around a 0.150 inch outer diameter mandrel 20 in an opposite helix configuration. The second sinusoidal wave form 25 is slid over the first sinusoidal wave form 15 and formed onto the 0.100 inch forming mandrel 20. The proximal ends of the first and second sinusoidal wave forms 15 and 25 may be attached to each other. The distal ends of the first and second sinusoidal wave forms 15 and 25 may also be attached to each other. The means of attachment include looping the end segments 30 together, twisting, biocompatible adhesive, welding or stamping.

The bidirectional helix configuration of the sinusoidal wave forms will provide additional vessel coverage and hoop strength as compared to a single sinusoidal wave form stent. First and second wave forms 15 and 25 are symmetrically placed over each other to form crossing points 65. This will allow even expansion of the balloon 35.

The stent 10 is further processed onto a 0.080 inch diameter forming mandrel 20 then onto a 0.065 inch diameter forming mandrel 20. The forming mandrel 20 sequence allows a gradual reduction in the stent 10 outer diameter. Although it is possible to go directly from a 0.150 inch outer diameter to a 0.065 inch outer diameter forming mandrel 20 and make an acceptable stent it is more difficult to do so.

Figure 2:
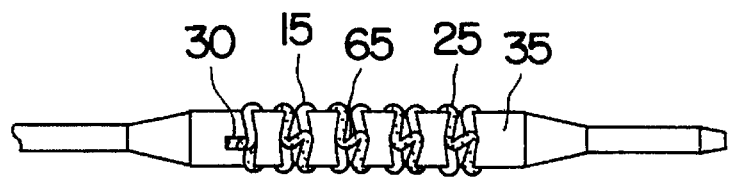
FIG. 2 is a side elevation view showing an overall view of a stent prosthesis fitted over a deflated balloon.
Figure 3:
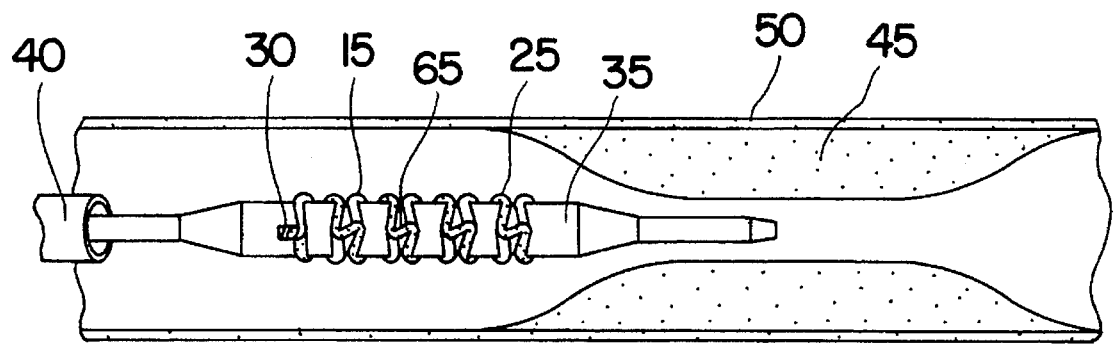
FIG. 3 is the balloon and stent assembly advanced within a vessel, approaching a partial occlusion.
Figure 4:
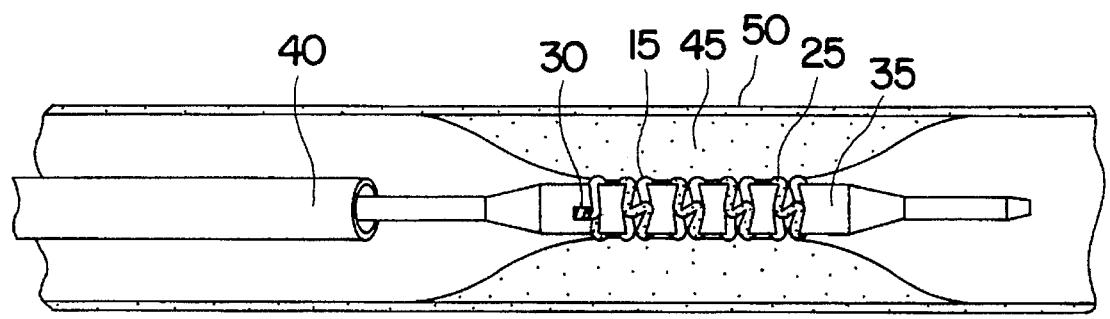
FIG. 4 is similar to FIG. 3 showing the balloon and stent assembly inside a partially occluded vessel.
Figure 5:
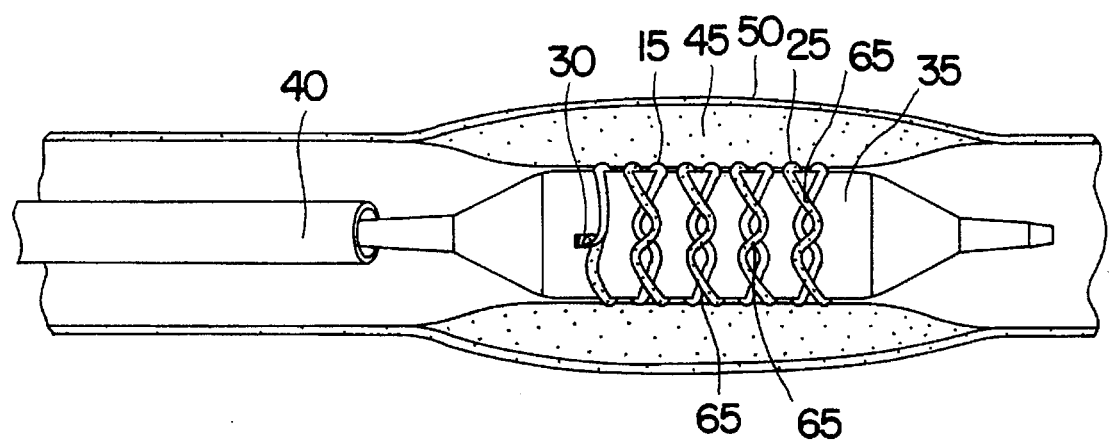
FIG. 5 is similar to FIG. 4 with the balloon inflated and the stent radially expanded illustrating an angioplasty procedure with a simultaneous deployment and implantation of a permanent prosthesis stent.
Figure 6:
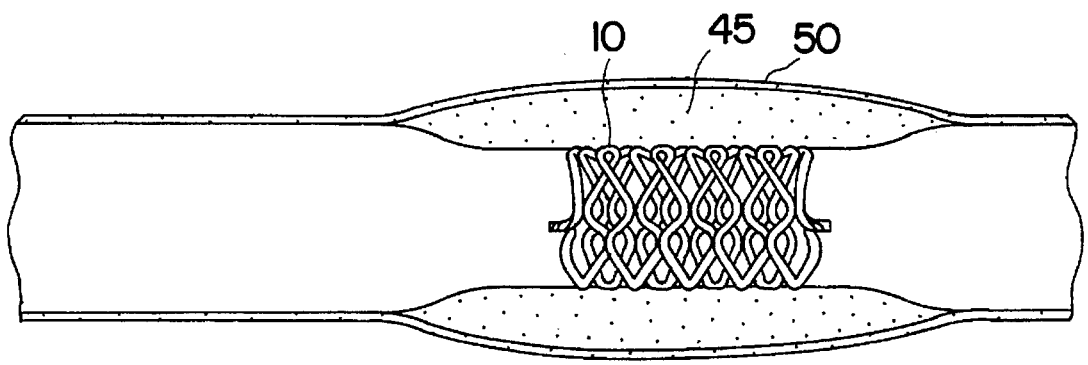
FIG. 6 is a view similar to FIG. 5 showing the plaque compressed and the prosthesis stent implanted and retained after removal of the balloon.

The stent 10 is removed from the mandrel 20 and placed over a suitable expandable diameter device such as an inflatable balloon 35 typically used for angioplasty procedures. A stent can be implanted during a single angioplasty procedure by using a balloon catheter bearing a stent 10 which has been crimped with a suitable crimping tool (not shown) onto the balloon 35 as shown in FIG. 2. Manually squeezing the stent 10 over the balloon 35 is also acceptable. FIG. 3 shows how the balloon 35 and stent 10 assembly emanate from a guiding catheter 40 inside vessel 50 and are advanced toward a partial occlusion 45. Once the balloon 35 is lodged in the stenosis 45 as seen in FIG. 4, the balloon 35 can be inflated as in FIG. 5 using standard angioplasty procedures and techniques. Stent 10 is thereby radially expanded as the balloon 35 is inflated, causing the stent 10 to contact the body lumen thereby forming a supporting relationship with the vessel walls as seen in FIG. 6. As balloon 35 expands, so does stent 10. The expanding balloon 35 together with the stent 10 compresses the plaque 45 in the stenosis and prevents possible reocclusion. When the angioplasty procedure is completed, balloon 35 is deflated and withdrawn leaving stent 10 firmly implanted within vessel 50. Previously occluded vessel 50 is recannalized and patency is restored. FIG. 6 shows stent 10 firmly implanted and imbedded in compressed plaque 45, providing both adequate support as well as a smooth lumen void of protrusions. Any protrusions are conducive to turbulent blood flow and potential formation of thrombosis.

The first and second sinusoidal wave forms 15 and 25 can have a diameter of 0.001 inches to 0.015 inches. A typical 10 ranges from 5 mm to 50 mm in length. The first and second sinusoidal wave forms 15 and 25 can be made of a low memory level metal such as tantalum, the preferred embodiment. Other acceptable materials include, stainless steel, titanium ASTM F63-83 Grade 1 or high carat gold K 19–22. A copper alloy, typically 110, when properly coated with polyester or Teflon® can also be used. Titanium and gold are biologically compatible and inert requiring no special coating or other treatment.

A problem with solid tantalum stents is that they may glow too brightly under fluoroscopy making it difficult to see the stent edges. One solution is to use clad materials. Clad materials are composed of one alloy on the outside and another alloy on the inside. With this design, a radiopaque material such as tantalum could be used on the inside. A higher strength material, such as stainless steel or a superalloy such as MP-35N, could be used on the outside thereby reducing the brightness of the tantalum. Applicant tested using three 0.005 inch wire diameter stent samples. The first sample comprised: a tantalum control sample with more than 99.7 weight % tantalum. The second sample comprised a stainless steel 316 clad alloy with 25% tantalum by volume. The third sample comprised an MP-35N clad alloy with 33% tantalum by volume. Each of the three wire samples were wrapped around a plastic test tube approximately ½ inches in diameter. An 80 KV heart grid simulating the density of a human thorax was placed between the fluoroscopy energy source and the wire samples. The third sample proved the most suitable given that the first sample was too bright with less well defined edges and the second sample was somewhat dim.

As shown in FIG. 2, stent 10 is centrally located and positioned with respect to the length of balloon 35. The first and second sinusoidal wave form 15 and 25 turns are evenly spaced so that when the stent 10 is expanded as shown in FIG. 5, the stent 10 will provide even support inside vessel 50, and resist external loading.

Figure 7:
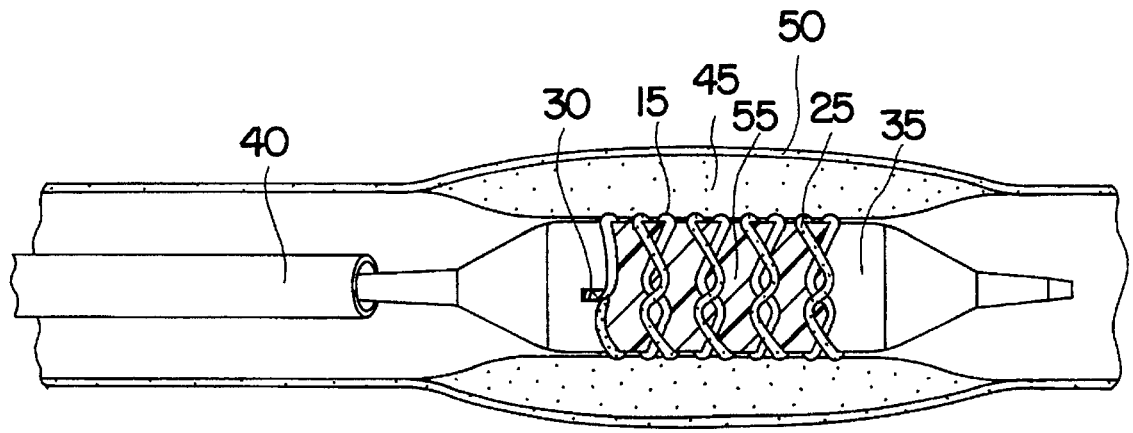
FIG. 7 is a side elevation view of an alternative embodiment of a stent incorporating a polymeric film.
Figure 8:
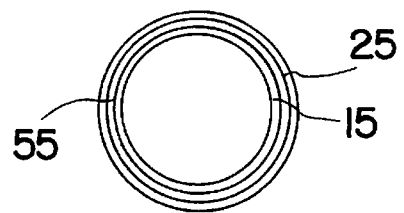
FIG. 8 is a cross-section of the stent of FIG. 7.
Figure 9:
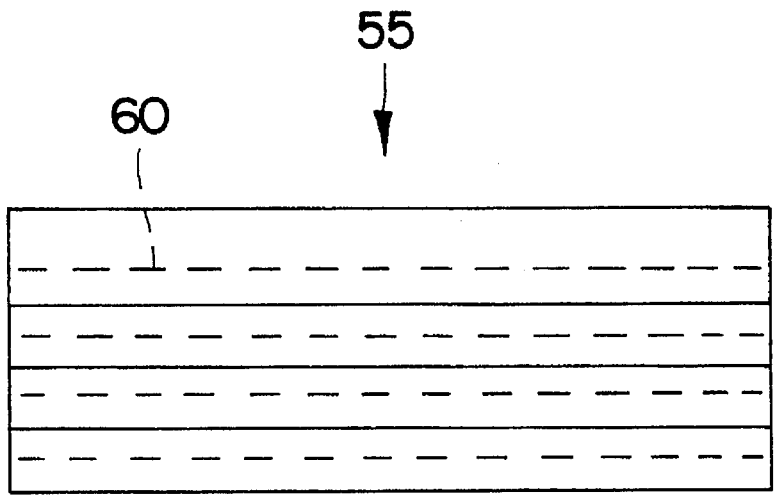
FIG. 9 is a side elevation view of the polymeric film of FIG. 7 in its folded form.
Figure 10:
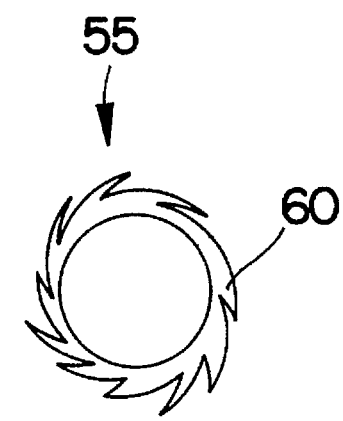
FIG. 10 is a cross-section view of the polymeric film of FIG. 9.

An alternative embodiment of the invention can be seen in FIGS. 7 and 8 wherein a film layer 55 is placed between the first sinusoidal wave form 15 and the second sinusoidal wave form 25. This design allows a more secure placement of the film layer 55 because of the internal and external metallic support structures comprising the first and second sinusoidal wave forms 15 and 25. The film 55 is flexible and preferably an elastic or stretchable material that is capable of conforming to the movements of the metallic stent 10 elements when expanded into contact with a body lumen. Fibrin film layer 55 materials would have a wall thickness of about 0.005 inches. Polymeric, natural biomaterial or other biocompatible materials could be used. Bioabsorbable polymers into which a therapeutic drug is compounded would be advantageous. By using an appropriate material the film 55 embodiment could be used for drug or gene therapy comprising a site specific delivery system. Therapeutic drugs could include antiplatelet drugs, anticoagulant drugs, anti-inflammatory drugs, antimetabolite drugs, re-stenosis limiting drugs and combinations thereof. The film 55 could also be folded into a longitudinal direction thereby forming pleats 60 to allow expansion as the balloon 35 is inflated as seen in FIGS. 9 and 10. The size and number of pleats 60 would depend on the size to which balloon 35 will be expanded. Vascular stents 10 typically have an outside diameter less than 0.075 inches and are radially expandable to approximately three times its original diameter.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|-----|-----------|
| 10 | Stent |
| 15 | First Sinusoidal Wave Form |
| 20 | Mandrel |
| 25 | Second sinusoidal Wave Form |
| 30 | End Segment Loop |
| 35 | Balloon |
| 40 | Guide Catheter |
| 45 | Plaque |
| 50 | Vessel |
| 55 | Film |
| 60 | Pleats |
| 65 | Crossing Points |

What is claimed is:

1. A radially expandable stent for implantation within a body vessel, comprising:

a first wire formed winding having a hollow cylindrical shape, the first winding including a preformed sinusoidal wave form pattern, the first winding being wound into a continuous helix the length of the stent, the first winding having a proximal end, a distal end and an outer diameter;

a second wire formed winding having a hollow cylindrical shape, the winding including a preformed sinusoidal wave form pattern, the second winding being wound into a continuous helix the length of the stent, the second winding helix being opposite that of the first winding helix, the second winding having a proximal end, a distal end and an inner diameter, the second winding having a greater inner diameter than the outer diameter of the first winding, the second winding being coaxial with the first winding;

the proximal end of the first winding being attached to the proximal end of the second winding and the distal end of the first winding being attached to the distal end of the second winding; and a means within the first winding to expand the first and second winding.

2. The stent according to claim 1 wherein the wire is formed of a biocompatible low memory level metal.

3. The stent according to claim 1 wherein the wire is formed of a biocompatible clad alloy having a radiopaque material covered with a higher strength material.

4. The stent according to claim 1 wherein the wire is formed of MP-35N with at least 33% tantalum by volume.

5. The stent according to claim 1 wherein the wire is formed of a stainless steel alloy 316 with greater than 25% tantalum by volume.

6. The stent according to claim 1 wherein the means for expanding the first and second winding is an expandable balloon extending longitudinally within the first winding.

7. The stent according to claim 1 wherein a film is placed between the first and second windings.

8. The stent according to claim 7 wherein the film comprises a therapeutic substance.

9. The stent according to claim 7 wherein the film is selected from a group of polymeric materials, natural biomaterial or other biocompatible materials.

10. A radially expandable stent for imputation within a body vessel, comprising:

a first wire formed winding having a hollow cylindrical shape, the first winding including a preformed sinusoidal wave form pattern, the first winding being wound into a continuous helix the length of the stent, the first winding having a proximal end, a distal end and an outer diameter;

a second wire formed winding having a hollow cylindrical shape, the winding including a preformed sinusoidal wave form pattern, the second winding being wound into a continuous helix the length of the stent, the second winding helix being opposite that of the first winding helix, the second winding having a proximal end, a distal end and an inner diameter, the second winding having a greater inner diameter than the outer diameter of the first winding, the second winding being coaxial with the first winding;

the sinusoidal wave form pattern of the first winding symmetrically intersecting with the sinusoidal wave form pattern of the second winding to form a uniform series of crossings thereby permitting even expansion of the first and second windings;

the proximal end of the first winding being attached to the proximal end of the second winding and the distal end of the first winding being attached to the distal end of the second winding; and a means within the first winding to expand the first and second winding.

11. The stent according to claim 10 wherein the wire is formed of a biocompatible low memory level metal.

12. The stent according to claim 10 wherein the wire is formed of a biocompatible clad alloy having a radiopaque material covered with a higher strength material.

13. The stent according to claim 10 wherein the wire is formed of MP-35N with at least 33% tantalum by volume.

14. The stent according to claim 10 wherein the wire is formed of a stainless steel alloy 316 with greater than 25% tantalum by volume.

15. The stent according to claim 10 wherein the means for expanding the first and second winding is an expandable balloon extending longitudinally within the first winding.

16. The stent according to claim 10 wherein a film is placed between the first and second windings.

17. The stent according to claim 16 wherein the film comprises a therapeutic substance.

18. The stent according to claim 16 wherein the film is selected from a group of polymeric materials, natural biomaterial or other biocompatible materials.

19. A radially expandable stent for implantation within a body vessel, comprising:

a first wire formed winding having a hollow cylindrical shape, the first winding including a preformed sinusoidal wave form pattern, the first winding being wound into a continuous helix the length of the stent, the first winding having a proximal end, a distal end and an outer diameter;

a second wire formed winding having a hollow cylindrical shape, the winding including a preformed sinusoidal wave form pattern, the second winding being wound into a continuous helix the length of the stent, the second winding helix being opposite that of the first winding helix, the second winding having a proximal end, a distal end and an inner diameter, the second winding having a greater inner diameter than the outer diameter of the first winding, the second winding being coaxial with the first winding; and a means within the first winding to expand the first and second winding.

20. A method for making a stent body for implantation within a body vessel comprising:

preforming a first wire into a sinusoidal wave pattern, the first wire having a proximal end and a distal end;

preforming a second wire into a sinusoidal wave pattern, the second wire having a proximal end and a distal end;

winding the preformed first wire on a cylindrical first mandrel such that the sinusoidal wave pattern is retained;

winding the preformed second wire on a cylindrical second mandrel such that the sinusoidal wave pattern is retained, the second mandrel having a larger outer diameter than the first mandrel;

removing the second wire from the second mandrel and sliding the second wire over the first wire;

attaching the proximal end of the first winding to the proximal end of the second winding; and attaching the distal end of the first winding to the distal end of the second winding.

21. The method according to claim 20 which includes the step of placing a film between the first and second wire.

22. A method for making a stent body for implantation within a body vessel comprising:

preforming a first wire into a sinusoidal wave form pattern, the first wire having a proximal end and a distal end;

preforming a second wire into a sinusoidal wave form pattern, the second wire having a proximal end and a distal end;

winding the preformed first wire on a cylindrical first mandrel such that the sinusoidal wave pattern is retained;

winding the preformed second wire on a cylindrical second mandrel such that the sinusoidal wave pattern is retained, the second mandrel having a larger outer diameter than the first mandrel;

removing the second wire from the second mandrel and sliding the second wire over the first wire, the sinusoidal wave form pattern of the first winding symmetrically intersecting with the sinusoidal wave form pattern of the second winding to form a uniform series of crossings thereby permitting even expansion of the first and second windings;

attaching the proximal end of the first winding to the proximal end of the second winding; and attaching the distal end of the first winding to the distal end of the second winding.

23. The method according to claim 22 which includes the step of placing a film between the first and second wire.

* * * * *

UNITED STATES PATENT AND TRADEMARK OFFICE
CERTIFICATE OF CORRECTION

PATENT NO. : 5,613,981
DATED : March 25, 1997
INVENTOR(S) : Boyle et al.

It is certified that error appears in the above-indentified patent and that said Letters Patent is hereby corrected as shown below:

Col. 6, line 33: "imputation" should be "implantation"

Col. 1, line 56: "4,649,9221" should be "4,649,922"

Col. 4, line 16: "shown)onto" should be "shown) onto"

Col. 4, line 39: "typical 10" should be "typical stent 10"

Col. 4, Line 59: "comprised:" should be "comprised"

Signed and Sealed this

Thirtieth Day of September, 1997

Attest:

BRUCE LEHMAN

Attesting Officer

Commissioner of Patents and Trademarks